(12) United States Patent
Vetterlein

(10) Patent No.: US 8,922,642 B2
(45) Date of Patent: *Dec. 30, 2014

(54) DEVICE AND METHOD FOR CONTROLLING TEST MATERIAL

(75) Inventor: Thomas Vetterlein, Main (DE)

(73) Assignee: Illinois Tool Works Inc., Glenview, IL (US)

( * ) Notice: Subject to any disclaimer, the term of this patent is extended or adjusted under 35 U.S.C. 154(b) by 902 days.

This patent is subject to a terminal disclaimer.

(21) Appl. No.: 12/601,205

(22) PCT Filed: May 15, 2008

(86) PCT No.: PCT/US2008/063664
§ 371 (c)(1),
(2), (4) Date: Jan. 9, 2010

(87) PCT Pub. No.: WO2008/147702
PCT Pub. Date: Dec. 4, 2008

(65) Prior Publication Data
US 2010/0182422 A1    Jul. 22, 2010

(30) Foreign Application Priority Data
May 22, 2007 (DE) .......................... 10 2007 024 058

(51) Int. Cl.
| | | |
|---|---|---|
| H04N 7/18 | (2006.01) |
| B44C 1/14 | (2006.01) |
| G01N 21/91 | (2006.01) |
| B32B 15/04 | (2006.01) |
| G01N 27/84 | (2006.01) |
| B32B 7/04 | (2006.01) |

(52) U.S. Cl.
CPC ... B32B 7/04 (2013.01); B44C 1/14 (2013.01); G01N 21/91 (2013.01); B32B 15/04 (2013.01); G01N 27/84 (2013.01)

USPC .......... 348/128; 348/125; 348/126; 348/127; 382/100

(58) Field of Classification Search
CPC ... G01N 27/902; G01N 27/82; G01N 27/904; G01N 27/9046; G01N 27/023; G01N 27/72; G01N 27/90; G01B 7/34; G01B 7/24; G01R 33/12; G01R 33/028
USPC .................................... 348/125–131; 382/100
See application file for complete search history.

(56) References Cited

U.S. PATENT DOCUMENTS

| | | | | |
|---|---|---|---|---|
| 4,058,762 A * | 11/1977 | Holt et al. | ...................... | 324/216 |
| 5,003,831 A * | 4/1991 | Link et al. | .................... | 73/865.9 |
| 5,410,521 A * | 4/1995 | Osato | ......................... | 369/13.14 |
| 6,626,047 B1 * | 9/2003 | Vetterlein | ........................ | 73/800 |
| 2002/0168099 A1 * | 11/2002 | Noy | .............................. | 382/149 |

(Continued)

FOREIGN PATENT DOCUMENTS

| | | |
|---|---|---|
| DE | 3106803 A1 | 9/1982 |
| DE | 3440473 A1 | 5/1986 |

(Continued)

OTHER PUBLICATIONS

Database WPI Week 200361, Thomson Scientific, London, GB, AN 2003-646658, XP-002493687.

(Continued)

*Primary Examiner* — Duyen Doan
(74) *Attorney, Agent, or Firm* — Lowe Hauptman & Ham LLP

(57) ABSTRACT

The invention relates to apparatus monitoring test media used in or applicable to magnetic testing, said apparatus comprising a test element fitted with an artificial defect and a test medium feed and a test return as well as a magnetic field generator, further a magnetic field adjustment unit to adjust the magnetic field strength acting on the test element and/or the artificial defect, being adjustable at different magnetic field intensities to check the test medium, and to a corresponding method.

9 Claims, 2 Drawing Sheets

(56) References Cited

U.S. PATENT DOCUMENTS

Figure 1:
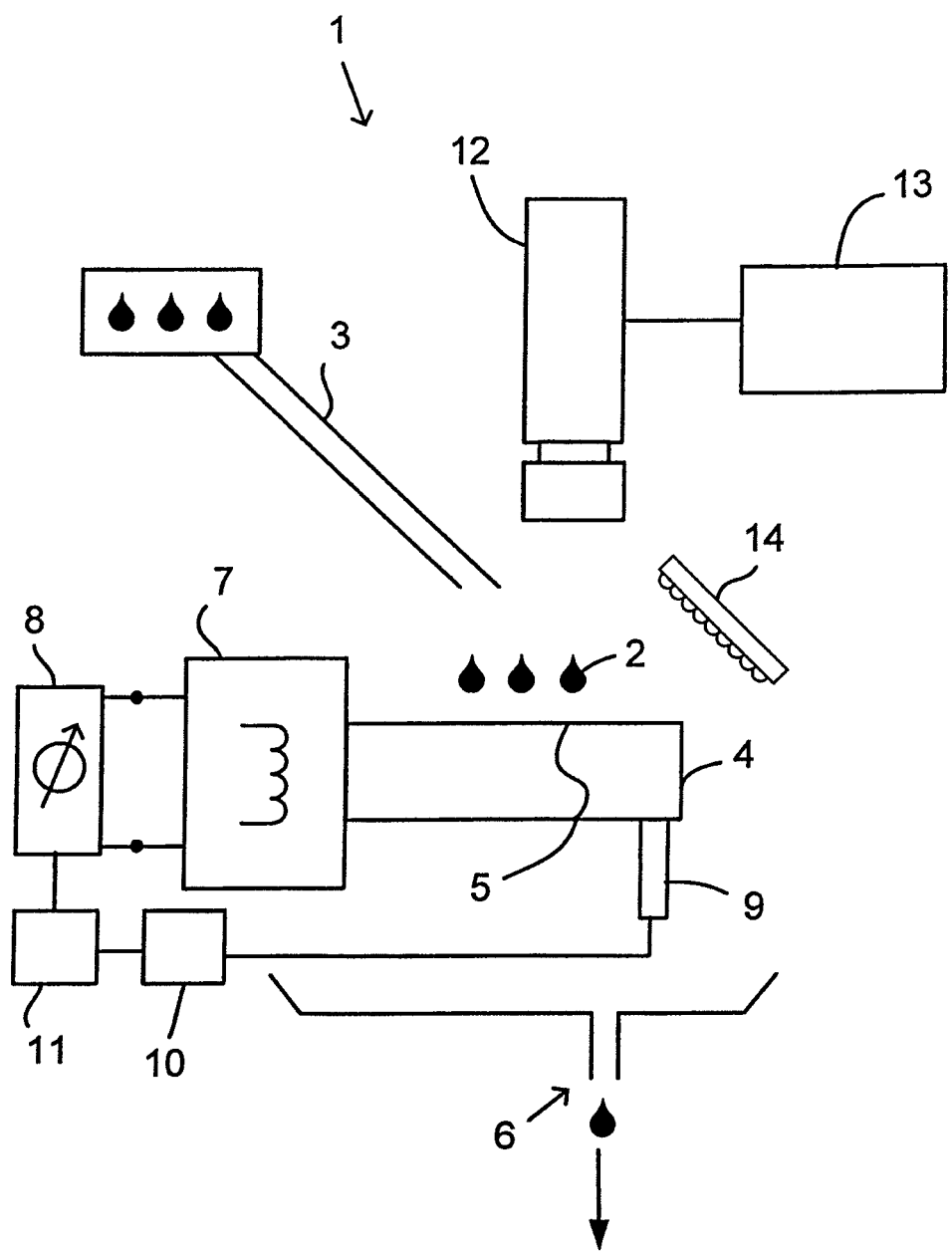

| | | | |
|---|---|---|---|
| 2003/0010093 A1* | 1/2003 | Barjesteh | 73/40 |
| 2006/0029257 A1* | 2/2006 | Eguchi et al. | 382/108 |
| 2006/0033504 A1* | 2/2006 | Barber et al. | 324/523 |
| 2006/0078193 A1* | 4/2006 | Brummel et al. | 382/152 |
| 2006/0133660 A1* | 6/2006 | Ogi et al. | 382/149 |
| 2007/0013370 A1* | 1/2007 | Nakano et al. | 324/232 |
| 2010/0142753 A1* | 6/2010 | Vetterlein | 382/100 |

FOREIGN PATENT DOCUMENTS

| | | | |
|---|---|---|---|
| DE | 3602395 A1 | 7/1987 |
| DE | 3907732 A1 | 9/1990 |
| JP | 2001281226 A | 10/2001 |

OTHER PUBLICATIONS

Database WPI Week 200719, Thomson Scientific, London, GB, AN 2007-189233, XP-002493688.

Database WPI Week 200214, Thomson Scientific, London, GB, AN 2002-100340, XP002493689.

DE Search Report for 10 2007 024 058.0 dated Sep. 26, 2007.

ISR and WO for PCT/US2008/063664 dated Sep. 5, 2008.

* cited by examiner

DEVICE AND METHOD FOR CONTROLLING TEST MATERIAL

RELATED APPLICATIONS

The present application is a national phase of PCT/US2008/063664 filed May 15, 2008, and claims priority from German Application Number 102007024058.0 filed May 22, 2007, the disclosures of which are hereby incorporated by reference herein in their entirety.

The present invention relates to a device/apparatus monitoring test materials/media which are used in magnetic testing, also to a method monitoring such test media.

Magnetic testing (MT) or magnetic particle inspection (MPI) procedures presently are widely used in magnetic workpiece quality control. In such tests the workpieces are exposed (magnetized) to a magnetic field, then they are wetted/rinsed with a test medium suspension. The test medium suspension contains a powder or a grain-like (in particular ferromagnetic) material which can be arranged in place by a magnetic field and which is clad by a substance (fluorescing when exposed to uv) or imbedded in said substances. Material defects, in particular cracks in the workpiece being tested when being magnetized cause stray fields at the sites of said defects. These stray fields attract testing material which collects at the defect sites and which thus is concentrated there, resulting in a localized concentration of testing material (such localized concentration is often shaped like a caterpillar). When exposed to uv, such aggregates of testing material may be made to fluoresce, as a result of which the workpiece defects can be well identified.

The test medium suspension is subjected to wear and/or aging during workpiece quality control. The loss of material shifts the ratio of liquid in the suspension to the cladding substance actively contributing to defect display toward higher liquid proportions. The mechanical stresses applied to the test medium also separate the ferromagnetic material from its optically active cladding substance, whereby, when the test medium suspension is used for extended times, the magnetic particles may still be clinging to the defect zones and cause localized concentrations of the particles, on the other hand they may become less uv-detectable with time.

Because of such test medium aging/wear, the test medium condition must be monitored, i.e. tested, to assure it still assures reliable workpiece defect detection, or to indicate the test medium must be changed.

The German patent document DE 190 39 725 B4 discloses a pertinent method and apparatus for automated test medium monitoring. The test medium's status check or monitoring takes place in an apparatus wherein the test medium being monitored is drained from a bypass conduit into the test medium circuit of said apparatus and is then tested for its condition. This apparatus includes a ferromagnetic test element fitted with several artificially/deliberately applied reference cracks, further a coil generating a magnetic field applied to the test element, and a source of uv. A glass tube is configured on the test element at its side opposite the reference crack and serves to pass the suspension, i.e. the test medium to be checked. The glass tube being permeable to magnetic fields, and the cracks generating stray fields causing accumulations of ferromagnetic particles, then following magnetization, or after the final wetting of said tube, said material accumulation displayed as a localized concentration of ferromagnetic particles will have taken place, which can be driven into fluorescence after being uv irradiated.

On the top of the tube are configured photodiodes detecting the luminous displays constituted by the test medium concentrations respectively a test reflector, each photodiode being associated with one test crack respectively the test reflector. The luminous intensity of all crack displays and of the test reflector is transduced, using a focusing optics and a photo element of the photodiodes, into an electrical value which shall be stored and then used for rating. Because only one brightness respectively intensity signal can be generated for each test, the accuracy offers by this automated measurement is correspondingly low. Moreover any test medium residually present and away from the magnetic field concentration may introduce errors because able to affect the intensities during uv irradiation.

Accordingly it is the objective of the present invention to create a test-medium monitoring apparatus used/applicable in magnetic testing and assuring that monitoring shall show reliably that the test medium is still of appropriate quality for magnetic testing. Another objective of the present invention is to create a method also assuring that the test medium quality is appropriate.

Said objectives are met by a test-medium monitoring apparatus applicable to magnetic testing procedures as detailed herein.

The present invention is illustratively elucidated in the following modes of implementation and in relation to the appended drawings.

Figure 2:
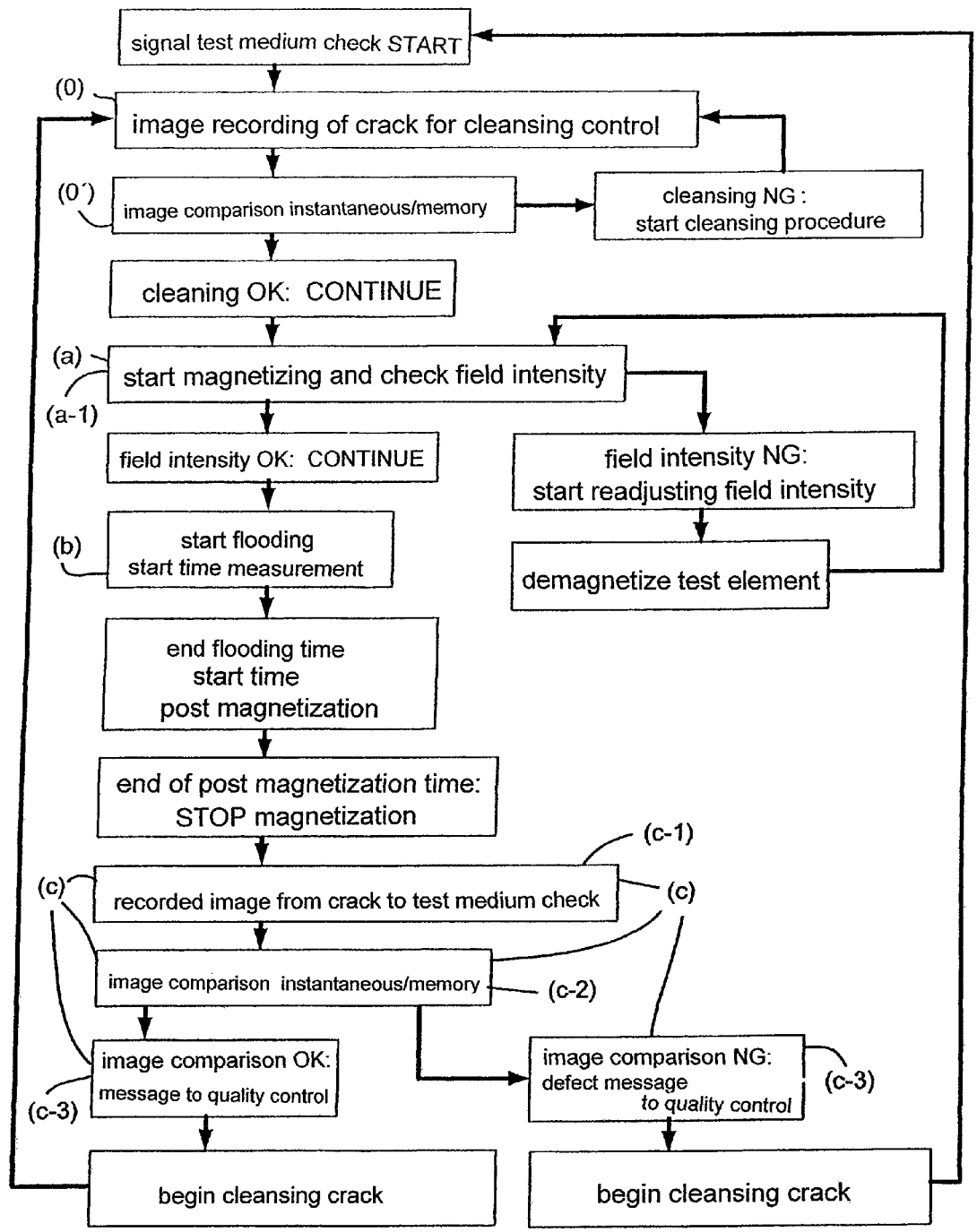

FIG. 1 schematically shows a preferred embodiment mode of the apparatus of the invention, and FIG. 2 is a flow diagram of a preferred mode of implementation of the method of this invention.

As shown in FIG. 1, an apparatus 1 monitoring a test medium 2 used in magnetic testing comprises a test medium feed 3, a test element 4 fitted with an artificial, reference defect in the form of a crack 5 and a test medium return 6 in the form of a collecting pan fitted with a drain. The test medium feed 3 floods the test element 4 and the crack 5 with test medium 2 which is subsequently evacuated through the said return 6.

In the present, preferred embodiment mode of the invention, the test medium feed 3 and the test medium drain 6 constitute a bypass to a magnetic testing apparatus wherein workpieces, for instance motor vehicle or aircraft parts are checked for defects. The test medium 2 being monitored is a suspension of a liquid, preferably water or oil, and a powder or grain-like material which can be displaced by a magnetic field and which in a preferred embodiment mode consists of a ferromagnetic core covered by an optically active cladding. "Optically active" in this respect means that the cladding material will fluoresce when being irradiated with uv.

To generate a magnetic field acting on the test element 4, i.e. on the artificial reference defect in the form of a crack 5, the apparatus 1 furthermore comprises a magnetic-field generator in the form of a coil 7. The coil 7 is configured in a manner that the field lines of the magnetic field acting on the test element 4, respectively the crack 5, run perpendicularly to the longitudinal axis of the test element 4 and approximately parallel to the crack 5. To allow checking the test medium under actual conditions, that is when applying magnetic field intensities as required in the parallel-operating quality control or defect check of workpieces, the apparatus 1 is also fitted with a magnetic field adjustment unit 8 monitoring the test medium 2 and adjusting the magnetic field intensity applied to the test element 4 and/or the crack 5 to check the test medium at different magnetic field intensities. In general the adjusted magnetic field intensity corresponds to that used in the parallel-operating workpiece quality control.

To measure the magnetic field strength applied to the test element 4 or the crack 5, the apparatus 1 includes a magnetic field sensor. In the shown preferred embodiment mode, said sensor is in the form a Hall generator 9. Alternatively to the Hall generator 9, a SQUID magnetometer may be used, or a device such as an ohmmeter, making use of the phenomenon of "giant magnetoresistance". In the preferred embodiment mode, the Hall generator makes contact with test element 4 and, as already cited, measures magnetic field intensity acting on the test element i.e. on the crack 5. The magnetic sensor (Hall generator 9) communicates through an associated magnetic field analyzer 10 analyzing the values of the magnetic field applied to the test element 4/crack 5. At equal time intervals, the magnetic field analyzer measures the magnetic field applied to the test element 4/crack 5. Alternatively the applied field also might be monitored continuously. The magnetic field control 11 compares the magnetic field applied to the test element 4/crack 5 with a magnetic field predetermined by the magnetic-adjusting unit 8 to readjust by means of said unit 8 the magnetic field in the event the measured field strength should be outside a predetermined field strength interval, where this interval lies in general about the predetermined value from said magnetic adjusting unit 8.

In the above described embodiment mode, all interfaces, including those between the magnetic field sensor (Hall generator 9) and the magnetic field analyzer 10 and between the magnetic field analyzer 10 and the magnetic field control 11, are USB interfaces. Obviously any other interface, for instance IEEE or RS 232, or a combination of different interfaces, including wireless communication, may be used.

It should be borne in mind that the crack 5 is introduced by spark or laser erosion into the test element 4. To attain reliable defect detection, the dimensions of the crack 5 match/correspond to the lower-limit defects to be expected in the workpiece.

To rate the cleanliness of the test element 4 prior to the test medium check and the condition of the test medium 2, the apparatus 1 also comprises an image recorder in the form of a CCD camera 12 and an image analyzer 13. The CCD camera generates an image of at least some parts of the test element 4 that contain at least portions of the crack 5. The images generated by the CCD camera 12 then are rated in then image analyzer 13. For that purpose and as regards the preferred embodiment mode of the invention, both the CCD camera 12 and the image analyzer 13 are fitted with a USB interface to assure problem-free communication between the CCD camera and the analyzer.

In the preferred embodiment mode of the invention, the image analyzer 13 comprises an image comparator comparing the image generated by the CCD camera 12 with a reference image stored in a reference image memory. Alternatively or additionally to image comparison, other optical analyses also may be carried out, such as line monitoring and/or procedure-based classifying algorithms. The CCD camera, which may be color or black and white, also may be replaced by an interlaced camera, a progressive scan camera, a CMOS camera (which allows high contrasts) or also an IEEE or an RS232 or also a serial or a parallel interface as well as a network interface or a wireless interface. The various components also may be integrated using a grabber card or firewire interface.

To assure reliable detection of the tell-tale increased flux concentration, i.e., the increased aggregate of material in the zone of the crack 5, the apparatus 1 moreover includes an illumination system in the form of UV LED's 14 of which a plurality are configured on a board. The radiation from the uv LED's excite the optically active particle claddings into fluorescence and in this manner generate an easily detected, easily analyzed signal. Mercury vapor or xenon vapor lamps also may be used as alternatives. Details relating to image analysis/comparison are elucidated below in the discussion of the method of the present invention.

Be it borne in mind that as regards image-based ratings compared to intensity-distribution based ratings, an actual, object-oriented decision criterion will be offered by the former. As a result, besides the intensity being considered, that rating also includes the contrasts and the shape of the increased flux concentration, further image based decision criteria, allowing thereby more accurate ratings and hence more accurate measurement of the test medium than is possible in the state of the art.

Moreover the magnetic field adjusting unit 8 and the image analyzer 13, while being described being in combination in the above discussed preferred embodiment mode, also may be integrated each while being independent of the other in an apparatus 1 of the present invention. In other words, in another design, only one magnetic adjusting unit 8 or only one image analyzer 13 may be included in an apparatus 1.

A method of the present invention to monitor test media 2 takes place as follows (see flow diagram of FIG. 2).

In a stage (a), a magnetic field generated by the coil 7 is applied to the test element 4 fitted with the artificial, reference defect in the form of a crack 5. In a further stage (b), the test medium 2 is deposited at least on parts of the test element 4 for a predetermined time interval. During that time, in the preferred implementation of the present invention, the test element is flooded with the test medium suspension already described above. Next, in stage (c) rating the condition of the test medium 2 in the zone of the crack 5, the increase in test medium aggregation near the crack is ascertained. In the present invention, the magnetic field intensity acting on the test element 4 and/or the crack 5 is adjusted before and/or during the stage (a) [magnetization of the test element 4], as a result of which, during this stage (a) the magnetic field control 11 does adjust the magnetic field intensity, whereas before stage (a) sets in, both manual adjustment to a desired value and assumption of the desired value from outside the apparatus 1 (for instance from the workpiece quality control unit) are involved.

To control the magnetic field intensity, either during at least part or all of the stage (a), a sub-stage (a-1) shall be carried out, wherein the magnetic field intensity acting on the test element 4 and/or the crack 5 is measured by the magnetic field sensor in the form of the Hall generator 9. In the preferred mode implementation, the magnetic field intensity is measured at predetermined time intervals; however continuous or quasi-continuous measurements and ensuing continuous or quasi-continuous control of the magnetic field intensity are also appropriate.

If the applied magnetic field intensity is determined to be good (OK) at the end of stage (a), namely being within a predetermined range which is associated with an arbitrary predetermined and as a rule predeterminable value, then the deposition of the test medium 2—namely flooding with a test medium suspension—may begin for a predetermined time interval (stage (b)). If on the other hand the magnetic field intensity is determined to be poor (NG), the test element (4) must be demagnetized (before being flooded). Thereafter the method may be resumed by renewing the procedure of stage (a).

After said flooding, that is after stage (b) and prior to stage (c), the method of the invention includes a stage (b') of post-magnetizing the test element 4 during a predetermined time interval, the inflow of test medium being precluded during said stage (b') while the coil 7 however is operative during the post-magnetizing time interval, as a result of which the previously applied test medium 2 is drawn by the stray field caused by the crack 5 into said crack zone where it forms the areas of increased test medium concentration. Past this post-magnetizing stage, the increased material concentration in the area of the crack 5—as manifested by the increased local magnetic field intensity—is analyzed in stage (c) to rate the condition of the test medium 2.

In that procedure, the stage (c) comprises the following sub-stages: (c-1), which is the generation of an image of at least part of the test element comprising at least a portion of the crack 5, using the image recorder 12; (c-2), which consists of analyzing the image recorded by the image analyzer 13; and (c-3), rating the condition of the test medium 2 based on image analysis. In the preferred implementation of the method of the present invention, the image generated by the CCD camera 12 is compared in the image analyzer 13 containing the image comparator already cited in relation to the apparatus 1, in stage (c), with a reference image representing the same segment of the test element under the same external conditions (for instance illumination conditions) jointly with optimal increase in local magnetic flux.

Be it borne in mind that besides an image comparison as already cited in the discussion of apparatus 1, any other image analysis also is applicable. If the image analysis in the form of image comparison stays within given limits, i.e. the image comparison is found to be "OK", the quality control receives a message about the workpieces, and the control keeps operating continuously. If however the image comparison outcome is "no good" (NG), an error message is sent to the workpiece quality control which then is stopped to allow changing the test medium 2 in the entire facility.

In both instances, namely when the image comparison result is OK and NG, the message is followed by cleaning the test element 4 respectively the crack 5. For that purpose the test element 4 first is demagnetized by applying to it an oscillating, demagnetizing field generated by the coil 7, whereupon a test medium suspension is applied through the test medium feed 3 as a flooding means, as a result of which the zones of higher test medium concentration are entrained by the test medium suspension. A check on the cleansing, i.e. the cleanliness of the test element 4 with the crack 5 then takes place before there is new magnetization, that is before again implementing again stage (a).

Moreover an image from part of the test element 4 including at least a portion of the crack 5 is again generated in the CCD camera 12 in a stage (0). Said image is analyzed by the image analyzer 13 in a stage (0'). In the present preferred mode of implementation, such image analysis is carried out comparing recorded image of the cleansed test elements and the reference image with optimally shaped magnetic flux concentration. Alternatively, a second reference image might be stored that shows an optimally cleansed test element 4 and then the recorded image will be compared with the reference image.

Be it noted that in all instances where the image comparisons are OK, the instantaneous images, that is the images representing the last cleansing result respectively the last local increased magnetic flux density shall be discarded, whereas in the event of an NG image, it will be stored and hence recorded.

In the above described mode of implementation, image comparison always is relative to one and the same reference image showing an optimal caterpillar. When checking the cleanliness of the test element 4, the decision criterion therefore makes a decision based on any deviation between the two images, whereas the decision regarding the state of the test medium 2 is based on the largest possible congruence. Conceivably, however, the reference image alternatively also might be a clean test element 4 free of any spike in magnetic flux density or also two reference images, a clean one and one with the best possible magnetic flux density spike. Again a still larger number of references images might be used. In such an instance the comparison would show which reference state is the one closest to that of the test medium 2.

In the preferred mode of implementation, the reference image(s) is/are recorded/stored in the image comparator. When, in stage 0', image comparison shows that the cleanliness is outside predetermined limits, then the test element shall be cleansed again, and thereupon the stages (0) and (0') are repeated, that is the cleanliness of the crack is rated again.

It must be stressed that the method of the present invention already includes in its basic concept that the adjustability of the magnetic field, namely magnetizing the test element 4 and the crack 5, and also analysis using an image analyzer 13, may be carried out independently from each other.

Even though the invention was described above having a given combination of features, it also covers further conceivable combinations.

The invention claimed is:

1. An apparatus for monitoring a test medium, the test medium being a powder which is displaceable in position by a magnetic field, said apparatus comprising
a test element having an artificial crack,
a test medium feed for feeding the test medium to the test element,
a test medium return to return the test medium, and
a magnetic field generator for generating a magnetic field to be applied to the test element,
an image recorder for generating an image of at least one part of the test element which contains at least one portion of the artificial crack, and
an image analyzer for rating the image generated by the image recorder, the image analyzer comprising an image comparator for comparing the image generated by the image recorder with a number of previously stored reference images to show a state of the test medium,
wherein the artificial crack is introduced by spark or laser erosion into the test element and the dimension of the artificial crack corresponds to lower-limit defects expected in the test element.

2. An apparatus as claimed in claim 1, wherein the image recorder is a USB compatible CCD camera.

3. An apparatus as claimed in claim 1, further comprising an illuminator to illuminate the test element during image generation.

4. An apparatus as claimed in claim 1, wherein the image comparator includes a reference memory to store the reference images.

5. A method of monitoring a test medium, the monitored test medium being a powder which is displaceable in position by a magnetic field, the method comprising:
magnetizing a test element having an artificial defect by applying a magnetic field generated by a magnetic field generator to the test element,
depositing the test medium on at least one part of the test element for a predetermined time interval, and
detecting an increased quantity of the test medium in a zone of the artificial defect to ascertain a physical condition of the test element, wherein said detecting comprises:
generating an image of the at least one part of the test element having at least one portion of the artificial defect using an image recorder,
analyzing the image generated by the image recorder using an image analyzer by comparing the image generated by the image recorder with a number of previously stored reference images, to show a state of the test medium, and rating the physical condition of the test element based on the image analysis, wherein the artificial crack is introduced by spark or laser erosion into the test element and the dimension of the artificial crack corresponds to lower-limit defects expected in the test element.

6. The method as claimed in claim 5, further comprising, prior to said magnetizing generating an image of at least one part of the test element with at least one portion of the artificial defect using the image recorder, and rating the image using the image analyzer, in order to ascertain a degree of cleanliness of the test element.

7. The method as claimed in claim 6, further comprising, when the degree of cleanliness of the test element is outside a predetermined limit, cleansing the test element is carried out, and repeating said generating and rating before said magnetizing.

8. An apparatus as claimed in claim 3, wherein the illuminator is UV LEDs.

9. An apparatus as claimed in claim 1, wherein the magnetic field generator is configured to generate the magnetic field with field lines that run perpendicularly to a longitudinal axis of the test element.

* * * * *